United States Patent [19]

Hallgren et al.

[11] 4,184,847
[45] Jan. 22, 1980

[54] METHOD OF INDICATING RHEUMATOID FACTORS

[75] Inventors: Henning R. Hällgren, Upplands-Bälinge; Leif E. Wide, Uppsala, both of Sweden

[73] Assignee: Pharmacia Diagnostics AB, Uppsala, Sweden

[21] Appl. No.: 818,647

[22] Filed: Jul. 25, 1977

[30] Foreign Application Priority Data

Sep. 8, 1976 [SE] Sweden .............................. 7609905

[51] Int. Cl.² ............................................ G01N 33/16
[52] U.S. Cl. ................................. 23/230 B; 23/230.6; 23/915; 424/1; 424/8; 424/12
[58] Field of Search .................... 23/230 B; 424/8, 12, 424/1

[56] References Cited

U.S. PATENT DOCUMENTS

| 3,594,466 | 7/1971 | Lille | 424/12 |
| 3,658,982 | 4/1972 | Reiss | 424/12 |
| 3,689,632 | 9/1972 | Mizushima | 424/12 |
| 4,062,935 | 12/1977 | Masson | 424/12 |

OTHER PUBLICATIONS

John S. Cowdery, Jr. et al., J. Immunol., 114(1), 5-9 (Jan. 1975).
Chemical Abstracts, 71:58955x (1969).
Chemical Abstracts, 74:2303c (1971).

Primary Examiner—Sidney Marantz
Attorney, Agent, or Firm—Fred Philpitt

[57] ABSTRACT

A method of indicating rheumatoid factors, primarily such rheumatoid factors which belong to immunoglobulin classes other than the immunoglobulin class IgM, in an aqueous sample. The sample is reacted in the presence of the complement factor C1q in non-bound form with soluble, aggregated immunoglobulin labelled with one or more analytically indicatable atoms or groups to selectively precipitate such rheumatoid factors which, in the presence of C1q, are able to precipitate aggregated immunoglobulin, whereafter the analytically indicatable atoms or groups are indicated in the precipitation phase and/or in the solution.

3 Claims, No Drawings

METHOD OF INDICATING RHEUMATOID FACTORS

The present invention relates to a method of indicating rheumatoid factors.

Anti-immunoglobulins are also designated rheumatoid factors and can belong to the immunoglobulin classes IgM, IgG, IgA or, possibly, also to other immunoglobulin classes. Rheumatoid factors can, in turn, be directed against immunoglobulins belonging to the classes IgG or IgM, or possibly to other immunoglobulin classes, which immunoglobulins have been changed in structure due to immune complex formation or aggregation.

Earlier proposed test methods for indicating rheumatoid factors are based on the agglutination of, for example, blood corpuscles or latex particles coated with IgG. These methods primarily indicate rheumatoid factors of IgM-type directed against changed IgG. Most patients suffering from rheumatoid arthritis are positive in such a test, although 20–30% are negative.

According to the present invention there is now provided a method for the indication of rheumatoid factors in an aqueous sample in which the primary intention is to indicate other rheumatoid factors than those belonging to the immunoglobulin class IgM and which it has been impossible in the previously known methods to indicate to the extent desired.

The method according to the invention is characterised by the fact that the sample is reacted in the presence of complement factor C1q in non-bound form with soluble aggregated immunoglobulin labelled with one or more analytically indicatable atoms or groups to a selective precipitation of such rheumatoid factors which, in the presence of C1q, are able to precipitate aggregated immunoglobulin, whereafter the analytically indicatable atoms or groups are indicated in the precipitation phase and/or in the solution.

By complement factor C1q in non-bound form is meant that said factor shall not be bound to other C1 components.

This can be effected, for example, by adding a calcium-binding substance of the type ethylene diamine tetraacetic acid (EDTA) and other substances capable of binding calcium ions to form complexes. Normally the complement factor C1q is present in the sample in sufficient quantities. Should this not be so a negative control serum with liberated C1q can be added or C1q produced, for example, according to Proc.Natl.Acad.Sci (USA) 69 (1972), 65, can be added.

Soluble aggregated immunoglobulin can be produced, for example, by heating a solution of an immunoglobulin or by chemical treatment with bis-diazotized benzidine or di-(4-aminophenyl)-sulphone (cf. Handbook of Experimental Immunology, Second Ed. Edited by D. M. Weir, Blackwell Scientific Publications, Oxford, 1976, page 19.75) and subsequently separating soluble, aggregated immunoglobulin from monomeric immunoglobulin and from possibly formed minor quantities of insoluble aggregates by gel filtration techniques. Preferably, the immunoglobulin used in this context is belonging to the IgG class. The immunoglobulin is not aggregated more than that the major portion of the aggregated immunoglobulin is still soluble in the aqueous sample.

For labelling the aggregated immunoglobulin, there can be used any analytically indicatable atom or group known with regard to the labelling of immunoglobulins. Thus, the aggregated immunoglobulin can be labelled with radioactive isotopes in a conventional manner, a suitable isotope, such as $^{125}I$, being used (see for example the method accordng to Hunter and Greenwood, Nature, Volume 194, 1962, page 495). Similarly, the aggregated immunoglobulins can be labelled with a fluorescent group in a conventional manner, for example with the aid of a fluorescein derivative, such as fluorescein isothiocyanate. The aggregated immunoglobulins may also be labelled with enzymatically active groups or with groups containing free radicals suitable for indicating purposes.

The rheumatoid factors which can be indicated in this way belong primarily to the immunoglobulin classes IgG and IgA, while interference with such belonging to the class IgM is avoided. Rheumatoid factors belonging to the first mentioned classes are able to bind to aggregated immunoglobulin (for example aggregated IgG) to form a complex to which C1q can also be bound to form a larger complex of such magnitude as to cause precipitation.

The invention will now be described in more detail with reference to a specific example.

EXAMPLE

A. The preparation of aggregated human-IgG (agg IgG)

Human-IgG (fraction II from Cohn-fractionation) from combined human sera was obtained from Kabi AB, Sweden, and was heated in the form of a 2% IgG-solution for 20 minutes at 60° C. The thus obtained aggregated IgG (agg IgG) was separated from monomeric IgG by gel-filtration on a 90×1.5 cm column containing particles of dextran cross-linked with epichlorohydrin (Sephadex ® G-200 from Pharmacia Fine Chemicals AB, Sweden) and equilibrated with 0.1 M tris(hydroxymethyl)-aminomethane-HCl-buffer containing 0.5 M NaCl having a pH 7.4. Concentrations of the aggregated IgG were determined spectrophotometrically at 280 nm.

B. The preparation of labelled aggregated IgG

To 20 μl of a solution containing 40 μg aggregated IgG obtained in accordance with A above were added 500 μCi Na$^{125}$I and 10 μl 0.5 M sodium phosphate buffer having a pH 7.4 and 10 μg chloroamine T in 10 μl water. After 50 seconds 24 μg of sodium metabisulphite were added. The reaction mixture was separated on Sephadex ® G-200 (i.e. gel particles consisting of dextran cross-linked with epichlorohydrin), the first fraction with the void volume being recovered. The eluted labelled aggregated IgG was centrifuged at 3,500 g for 5 minutes to remove spontaneously precipitatable IgG. The labelled protein was diluted to approximately 40 μg/l (40,000 cpm in 0.1 ml) with a buffer solution prepared from 500 ml of 0.1 M sodium phosphate buffer having a pH 7.5, 500 ml of 0.15 M NaCl, 10 ml 5% (w/v) NaN$_3$ and 5 ml of Tween ® 20 (i.e. polyoxyethylene (20) sorbitan monolaurate).

C. Determination of rheumatoid factor-activity

Blood samples were taken as eptically from patients and permitted to clot at room temperature, whereafter they were centrifuged at 3,000 g and serum was recovered. The serum was diluted to 1:20 with a solution having the following composition: 500 ml of 0.1 M sodium phosphate buffer pH 7.5, 500 ml of 0.15 M NaCl, 1 ml of 1 M EDTA, 10 ml of 5% NaN$_3$, 5 ml of Tween ® 20. 200 μl of the serum dilution and 100 μl of I$^{125}$ labelled aggregate IgG (40,000 cpm) (obtained according to B) were charged to plastic tubes. The tubes were plugged and incubated under constant rotation for 16 hours at +4° C. The contents of the tubes were then centrifuged at 3,500 g for 3 minutes. The plastic plugs were removed and 2 ml of 0.9 M NaCl solution containing 0.5% of Tween ® 20 were added to each tube. The contents of the tubes were then centrifuged at 3,500 g for 3 minutes. The supernatant was then removed by suction. This washing procedure was repeated 3 times. The tubes were then plugged and placed in an automatic gamma counter.

It was found that high measurement values were obtained from samples obtained from patients suffering from rheumatoid arthritis or systemic lupus erythematosus which had rheumatoid factors belonging to the IgG and IgA classes, whilst conventional methods measuring rheumatoid factors belonging to the IgM class gave no indications.

What we claim is:

1. A method of indicating rheumatoid factors in an aqueous sample of human origin, said rheumatoid factors being other than those belonging to the IgM class, said method comprising:
   (a) treating said sample so that there is a presence of C1q in non-bound form,
   (b) reacting the treated sample with soluble, aggregated immunoglobulin labelled with one or more analytically indicatable atoms or groups to selectively precipitate such rheumatoid factors, and
   (c) thereafter measuring indicatable atoms or groups in the precipitated phase formed and/or in the solution.

2. A method according to claim 1 wherein the labelled aggregated immunoglobulin belong to the IgG class.

3. A method according to claim 1, wherein the aqueous sample of human origin is human serum.

* * * * *